United States Patent [19]

Thyes et al.

[11] 4,415,571

[45] Nov. 15, 1983

[54] CARBAMATE DIHYDROPYRIDAZINONES, THEIR PREPARATION AND THERAPEUTIC AGENTS CONTAINING THESE COMPOUNDS

[75] Inventors: Marco Thyes, Lugwigshafen; Albrecht Franke, Wachenheim; Horst Koenig; Dieter Lenke, both of Ludwigshafen; Hans D. Lehmann, Hirschberg-Leutershausen; Josef Gries, Wachenheim, all of Fed. Rep. of Germany

[73] Assignee: BASF Aktiengesellschaft, Fed. Rep. of Germany

[21] Appl. No.: 272,016

[22] Filed: Jun. 9, 1981

[30] Foreign Application Priority Data

Jun. 13, 1980 [DE] Fed. Rep. of Germany ....... 3022177
Sep. 8, 1980 [DE] Fed. Rep. of Germany ....... 3033702

[51] Int. Cl.³ .................. C07D 237/04; A61K 31/50
[52] U.S. Cl. .................................... 424/250; 544/239
[58] Field of Search .................... 424/250; 544/239

[56] References Cited

U.S. PATENT DOCUMENTS

| 3,475,431 | 10/1969 | Bachmann | 544/239 |
| 3,689,652 | 9/1972 | Curran | 424/250 |
| 3,806,509 | 4/1972 | Lebkuecher | 544/239 |
| 3,824,271 | 7/1974 | Allen, Jr. et al. | 260/465 D |
| 3,888,901 | 6/1975 | Allen, Jr. et al. | 260/465 R |
| 4,011,321 | 3/1977 | Coates et al. | 424/250 |

FOREIGN PATENT DOCUMENTS

| 113 | 1/1979 | European Pat. Off. ............ 544/239 |
| 1670158 | 12/1970 | Fed. Rep. of Germany . |
| 2150436 | 4/1972 | Fed. Rep. of Germany . |
| 2123246 | 11/1972 | Fed. Rep. of Germany . |
| 2157453 | 5/1973 | Fed. Rep. of Germany . |
| 2304977 | 8/1974 | Fed. Rep. of Germany . |
| 2727481 | 1/1979 | Fed. Rep. of Germany . |
| 53-124279 | 2/1978 | Japan . |
| 1404022 | 8/1975 | United Kingdom . |

*Primary Examiner*—Mark L. Berch
*Attorney, Agent, or Firm*—Keil & Witherspoon

[57] ABSTRACT

Novel 6-phenyl-4,5-dihydro-3(2H)-pyridazinones which are substituted in the p-position of the phenyl ring by a carbamate or thiocarbamate group, processes for their preparation, pharmaceutical formulations containing these compounds, and their use as drugs in thrombo-embolic disorders, and as anti-hypertensives.

4 Claims, No Drawings

CARBAMATE DIHYDROPYRIDAZINONES, THEIR PREPARATION AND THERAPEUTIC AGENTS CONTAINING THESE COMPOUNDS

The present invention relates to novel 6-phenyl-4,5-dihydro-3(2H)-pyridazinones which are substituted in the p-position of the phenyl ring by a carbamate or thiocarbamate group, to processes for their preparation, to pharmaceutical formulations containing these compounds, and to their use as drugs in thrombo-embolic disorders and as anti-hypertensives.

6-(Acylamino)-phenyl-4,5-dihydro-3(2H)-pyridazinones have been described in various publications. For example, German Laid-Open Application DOS No. 1,670,158 describes 6-(acylamino)-phenyl-4,5-dihydro-3(2H)-pyridazinones which are unsubstituted in the 4- and 5-positions and which have blood pressure-lowering and anti-inflammatory properties. German Laid-Open Application DOS No. 2,304,977 states that 6-phenyl-4,5-dihydro-3(2H)-pyridazinones which carry an alkyl group in the 4-position and are substituted in the p-position of the phenyl radical by a group of the formula —$NHR^4$, where $R^4$ is, for example, acyl or ethoxycarbonyl, have cardiovascular and antiphlogistic properties. German Laid-Open Application DOS No. 2,150,436 and U.S. Pat. Nos. 3,824,271 and 3,888,901 describe 5-alkyl-substituted 6-(alkanoylamino)-phenyl-4,5-dihydro-3(2H)-pyridazinones which lower the blood pressure. Further, German Laid-Open Application DOS No. 2,727,481 and German Patent Application No. P 28 54 191.5 discloses 6-(p-alkanoylaminophenyl)-4,5-dihydro-3(2H)-pyridazinones which are substituted in the alkanoyl group by one or more halogen atoms, and which can be used as drugs because of their thrombocyte aggregation-inhibiting and blood pressure-lowering properties.

German Laid-Open Application DOS No. 2,123,246 describes 6-(p-alkanoylaminophenyl)-4,5-dihydro-3(2H)-pyridazinones which carry a substituted amino group in the alkanoyl radical and which have a blood pressure-lowering, coronary-dilating and anti-inflammatory action. German Laid-Open Application DOS No. 2,157,453 states that 6-phenyl-4,5-dihydro-3(2H)-pyridazinones, which are substituted in the p-position of the phenyl radical by a group of the formula —NH-$CONR^5R^6$, where $R^5$ and $R^6$ are identical or different and each is, for example, hydrogen, alkyl or aryl, have cardio-vascular and anti-inflammatory properties. Finally, Japanese Patent Application No. 53,124-279 describes 6-[p-(alkoxycarbonylaminoalkyl)-phenyl]-4,5-dihydro-3(2H)-pyridazinones which have anti-allergic, membrane-stabilizing and thrombocyte aggregation-inhibiting effects.

We have found that 6-aryl-4,5-dihydro-3(2H)-pyridazinones of the general formula I

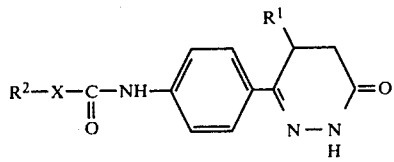

where X is oxygen or sulfur, $R^1$ is hydrogen or alkyl of 1 to 3 carbon atoms and $R^2$ is alkyl of 1 to 8 carbon atoms, which is unsubstituted or is substituted by one to four halogen atoms, by an alkoxy group of 1 to 4 carbon atoms, which is separated from X by not less than two carbon atoms, by a cycloalkyl group of 3 to 8 carbon atoms in the ring, which may or may not carry one or two alkyls of 1 to 3 carbon atoms, or by a phenyl radical which is unsubstituted or carries up to three identical or different substituents chosen from alkyl of 1 to 3 carbon atoms, alkoxy of 1 to 3 carbon atoms, halogen, trifluoromethyl or nitro, or is cycloalkyl of 3 to 8 carbon atoms in the ring, which is unsubstituted or substituted by up to four alkyls of 1 to 4 carbon atoms, or is alkenyl of 3 to 8 carbon atoms or alkynyl of 3 to 8 carbon atoms, or is phenyl which is unsubstituted or carries up to three identical or different substituents chosen from alkyl of 1 to 4 carbon atoms, alkoxy of 1 to 4 carbon atoms, halogen, trifluoromethyl, cyano and nitro, exhibit valuable pharmacological properties.

$R^1$ as alkyl of 1 to 3 carbon atoms is, in particular, methyl, ethyl or propyl.

$R^2$, as straight-chain or branched unsubstituted alkyl of 1 to 8 carbon atoms is, for example, methyl, ethyl, propyl, isopropyl, butyl, isobutyl, sec.-butyl, tert.-butyl, pentyl, 2-methylbutyl or isopentyl.

The preferred unsubstituted alkyl radicals $R^2$ are of one to four carbon atoms.

$R^2$ as straight-chain or branched alkyl of 1 to 8 carbon atoms which is substituted by up to four halogen atoms, such as chlorine, bromine or fluorine, is, for example, chloromethyl, bromomethyl, dichloromethyl, trifluoromethyl, 1-chloroethyl, 2-chloroethyl, 2-bromoethyl, 2-fluoroethyl, 1,2-dichloroethyl, 1,1,2-trichloroethyl, 2,2,2-trichloroethyl, 2,2,2-tribromoethyl, 2,2,2-trifluoroethyl, 2-bromopropyl, 3-chloropropyl, 2,3-dichloropropyl, 2,3-dibromopropyl, 3-bromo-2-chloropropyl, 2-chloroisopropyl, 2,2'-dichloroisopropyl, 2-chlorobutyl, 4-chlorobutyl, 1-chloromethylpropyl, 3,4-dibromobutyl, 2-chloroisobutyl or 3-chloroisobutyl.

Preferred haloalkyl radicals $R^2$ are of 1 to 4 carbon atoms and contain up to three halogen atoms, especially chlorine, bromine or fluorine.

Alkoxyalkyl radicals $R^2$, consisting of alkoxy of 1 to 4 carbon atoms linked to straight-chain or branched alkylene of 2 to 8 carbon atoms, the alkoxy group being separated from X by a chain of not less than two carbon atoms, are, for example, 2-methoxyethyl, 2-ethoxyethyl, 2-propoxyethyl, 2-isopropoxyethyl, 2-butoxyethyl, 2-methoxypropyl, 2-ethoxypropyl, 3-methoxypropyl, 3-ethoxypropyl, 2-methoxyisopropyl, 2-ethoxyisopropyl, 2-methoxybutyl, 3-methoxybutyl, 4-methoxybutyl and 1,1-dimethyl-2-methoxyethyl.

Preferably, the alkoxyalkyl radicals $R^2$ consist of alkoxy of 1 to 3 carbon atoms joined to alkylene of 2 to 4 carbon atoms.

$R^2$, as straight-chain or branched alkyl of 1 to 8 carbon atoms, which is substituted by cycloalkyl, of 3 to 8 carbon atoms in the ring, which may carry one or two alkyls of 1 to 3 carbon atoms, is, for example, cyclopropylmethyl, (1-methylcyclopropyl)-methyl, (2-methylcyclopropyl)-methyl, (2,3-dimethylcyclopropyl)-methyl, cyclobutylmethyl, (3-methylcyclobutyl)-methyl, cyclopentylmethyl, cyclohexylmethyl, 1-cyclopropylethyl, 1-cyclobutylethyl, 1-cyclopentylethyl, 2-cyclopropylethyl, 2-cyclobutylethyl, 2-cyclopentylethyl, 1-cyclopropylpropyl, 2-cyclobutylpropyl, 3-cyclopropylpropyl, 3-cyclopentylpropyl, 1-cyclopropyl-1-methylethyl, 2-cyclohexyl-1-methylethyl and 4-cyclohexylbutyl.

Preferred cycloalkylalkyl radicals $R^2$ are those consisting of unsubstituted or substituted cycloalkyl of 3 to 6 carbon atoms in the ring linked to alkylene of 1 to 3 carbon atoms.

$R^2$ as straight-chain or branched alkyl of 1 to 8 carbon atoms substituted by phenyl is, for example, benzyl, 1-phenylethyl, 2-phenylethyl, 1-phenylpropyl, 2-phenylpropyl, 3-phenylpropyl, 1-methyl-2-phenylethyl, 1-methyl-1-phenylethyl or 4-phenylbutyl.

Preferred phenylalkyl radicals $R^2$ consist of phenyl linked to alkylene of 1 to 4 carbon atoms.

Aralkyl $R^2$, which consists of phenyl which carries up to three identical or different substituents chosen from alkyl of 1 to 3 carbon atoms, eg. methyl, ethyl or propyl, alkoxy of 1 to 3 carbon atoms, eg. methoxy or ethoxy, halogen, eg. chlorine, bromine or fluorine, trifluoromethyl or nitro, linked to straight-chain or branched alkylene of 1 to 8 carbon atoms is, for example, o-methylbenzyl, m-methylbenzyl, p-methylbenzyl, p-ethylbenzyl, o-methoxybenzyl, m-methoxybenzyl, p-methoxybenzyl, o-ethoxybenzyl, m,p-dimethoxybenzyl, m,m',p-trimethoxybenzyl, o-chlorobenzyl, m-chlorobenzyl, p-chlorobenzyl, o-fluorobenzyl, m-fluorobenzyl, p-fluorobenzyl, m-trifluoromethylbenzyl, o-nitrobenzyl, p-nitrobenzyl, 1-(m-methoxyphenyl)-ethyl, 2-(m,p-dimethoxyphenyl)-ethyl, 2-(p-fluorophenyl)-ethyl or 2-(o-nitrophenyl)-ethyl.

Preferred aralkyl radicals $R^2$ consist of substituted phenyl linked to alkylene of 1 to 4 carbon atoms.

$R^2$ as cycloalkyl of 3 to 8 carbon atoms in the ring, which is unsubstituted or carries up to four alkyl radicals of 1 to 4 carbon atoms, eg. methyl, ethyl or propyl, is, for example, cyclopropyl, 1-methylcyclopropyl, 2-methylcyclopropyl, 1-ethylcyclopropyl, 2,2-dimethylcyclopropyl, 1,2,2-trimethylcyclopropyl, cyclobutyl, 1-methylcyclobutyl, 2-methylcyclobutyl, 3-methylcyclobutyl, 1-ethylcyclobutyl, 2-ethylcyclobutyl, 1,2-dimethylcyclobutyl, 2,2-dimethylcyclobutyl, 3,3-dimethylcyclobutyl, cyclopentyl, 1-methylcyclopentyl, 2-methylcyclopentyl, cyclohexyl or cycloheptyl.

The unsubstituted and substituted cycloalkyl radicals $R^2$ preferably are of 3 to 6 carbon atoms in the ring.

$R^2$ as alkenyl of 3 to 8 carbon atoms is, for example, allyl, but-2-enyl, but-3-enyl, 1-methylallyl, 2-methylallyl and pent-4-enyl.

Preferred alkenyl radicals $R^2$ are of 3 to 5 carbon atoms.

$R^2$ as alkynyl of 3 to 8 carbon atoms is, for example, prop-2-ynyl, but-2-ynyl, but-3-ynyl, 1-methylprop-2-ynyl, pent-2-ynyl, pent-4-ynyl, 1-methylbut-2-ynyl, 1-methylbut-3-ynyl or 1,1-dimethylprop-2-ynyl.

Preferred alkynyl radicals $R^2$ are of 3 to 5 carbon atoms.

Examples of $R^2$ as phenyl which carries up to three identical or different substituents chosen from alkyl of 1 to 4 carbon atoms, eg. methyl, ethyl or propyl, alkoxy of 1 to 4 carbon atoms, eg. methoxy or ethoxy, halogen, eg. chlorine, bromine or fluorine, trifluoromethyl, cyano or nitro are o-tolyl, m-tolyl, p-tolyl, p-ethylphenyl, o,p-dimethylphenyl, o,m,p-trimethylphenyl, o-methoxyphenyl, m-methoxyphenyl, p-methoxyphenyl, o-ethoxyphenyl, o-ethoxy-p-ethylphenyl, o-chlorophenyl, m-chlorophenyl, p-chlorophenyl, p-bromophenyl, p-fluorophenyl, m,p-dichlorophenyl, p-chloro-o-methylphenyl, m-trifluoromethylphenyl, p-cyanophenyl, o-nitrophenyl, m-nitrophenyl and p-nitrophenyl.

Preferred compounds are those where $R^1$ is hydrogen or methyl.

The dihydropyridazinones of the formula I are prepared by a process wherein an aminophenyl-dihydropyridazinone of the formula II

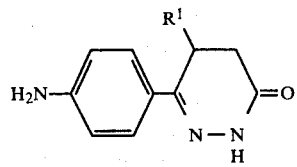

where $R^1$ has the meanings given for formula I, is reacted, in a conventional manner, with a compound of the formula III

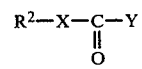

where X and $R^2$ have the meanings given for formula I, and Y is halogen, especially chlorine.

This reaction is carried out under conventional conditions, as a rule using not less than an equimolar amount of the haloformic acid ester or halothioformic acid S-ester of the formula III, advantageously in the presence of a solvent, and in the presence or absence of an auxiliary base as an acid acceptor, at from 0° to 140° C., preferably from 10° to 100° C., if appropriate at the boiling point of the reaction mixture and, where necessary, under pressure.

Suitable solvents are those which are inert under the reaction conditions, such as aromatic hydrocarbons, eg. benzene, toluene or xylene, cyclic aliphatic ethers, eg. tetrahydrofuran or dioxane, or dialkylformamides, eg. dimethylformamide. Auxiliary bases used as acid acceptors are, advantageously, inorganic bases, such as sodium carbonate or potassium carbonate, sodium bicarbonate or potassium bicarbonate, or tertiary organic amines, such as triethylamine.

According to another method of preparation, the novel dihydropyridazinones of the formula I are obtained if an aminoacid of the formula IV

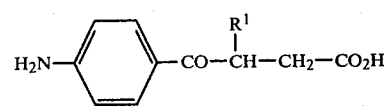

where $R^1$ has the meanings given for formula I, is reacted with a compound of the formula III

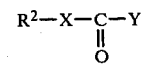

where $R^2$, X and Y have the meanings given above, and the resulting compound of the formula V

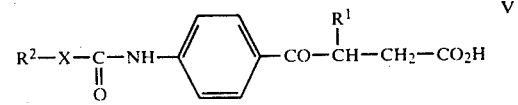

is cyclized with hydrazine.

The preparation of a compound of the formula V from an aminoacid IV and a haloformic acid ester or halothioformic acid S-ester III is carried out under the conditions described above for the reaction of an aminophenyl-dihydropyridazinone of the formula II with a compound of the formula III.

The cyclization of a compound of the formula V with hydrazine (preferably employed as the hydrate) is advantageously carried out in a solvent which is inert under the reaction conditions, especially a lower alcohol, eg. methanol, ethanol or propanol, a cyclic aliphatic ether, eg. tetrahydrofuran or dioxane, or a dialkylformamide, eg. dimethylformamide, at from 60° to 140° C., preferably from 80° to 120° C. As a rule, from 1 to 1.2 moles of hydrazine are used per mole of a compound of the formula V.

Compounds of the formula I can also be prepared by a process wherein an isocyanate of the formula VI

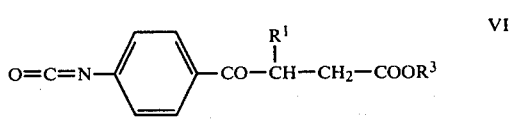

where $R^1$ has the meanings given for formula I and $R^3$ is alkyl of 1 to 3 carbon atoms, eg. methyl, ethyl or propyl, preferably methyl or ethyl, is reacted with a compound of the formula VII

where $R^2$ and X have the meanings given for formula I, and the resulting compound of the formula VIII

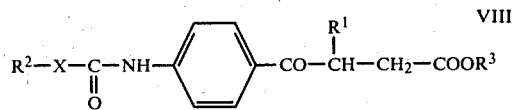

is cyclized with hydrazine.

The reaction of an isocyanate of the formula VI with a compound of the formula VII is carried out under conventional conditions, as a rule using not less than an equimolar amount of a compound of the formula VII, advantageously in the presence of a solvent, with or without addition of a catalyst conventionally employed for accelerating isocyanate reactions, at from 0° to 140° C., preferably from 20° to 120° C., if appropriate at the boiling point of the reaction mixture and, where necessary, under pressure.

Suitable solvents are those which are inert under the reaction conditions, such as aromatic hydrocarbons, eg. benzene, toluene or xylene, aliphatic or aromatic chlorohydrocarbons, eg. methylene chloride or chlorobenzene, cyclic aliphatic ethers, eg. tetrahydrofuran or dioxane, or dialkylformamides, eg. dimethylformamide. If the compound of the formula VII is liquid, the reaction can also be carried out in excess VII as the solvent.

Suitable catalysts for the reaction of an isocyanate of the formula VI with a compound of the formula VII are, for example, inorganic bases, such as sodium carbonate, potassium carbonate, sodium bicarbonate or potassium bicarbonate, alcoholates, eg. sodium methylate or potassium tert.-butylate, tertiary organic amines, eg. triethylamine, pyridine or 1,4-diazabicyclo[2.2.2]octane, or metal compounds, eg. lead-(IV), tin-(II), tin-(IV) or mercury-(II) compounds. Of the metal compounds used as catalysts, tin-(II), tin-(IV) and mercury-(II) compounds, such as tin octanoate, dibutyl-tin diacetate, dibutyl-tin dilaurate or phenyl-mercury acetate, are preferred.

The compounds of the formula II, and those of the formula IV, used as starting materials are known or can be prepared under the conditions described, for example, in German Laid-Open Application DOS No. 1,670,158 and DOS No. 2,150,436 or U.S. Pat. Nos. 3,824,271 and 3,888,901.

Amongst the isocyanates of the formula VI employed as starting materials, an example of a compound which is known is the compound where $R^1$ is hydrogen and $R^3$ is ethyl. Its synthesis is described in German Laid-Open Application DOS No. 2,157,453. The aminoacid of the formula IV, where $R^1$ is hydrogen, is first converted to the compound of the formula IX

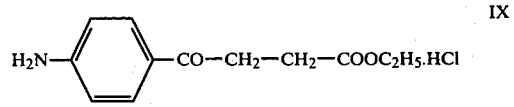

by treatment with ethanol and hydrogen chloride. IX is then reacted in a conventional manner with phosgene in a solvent which is inert under the reaction conditions, eg. toluene or xylene, to give ethyl 3-(p-isocyanatobenzoyl)-propionate (VI; $R^1$=H, $R^3$=—$C_2H_5$). Starting from the aminoacids of the formula IV, the other isocyanates of the formula VI can also be prepared by this process.

Examples of compounds according to the invention, which are obtained by the processes mentioned, are: 4,5-dihydro-6-(p-methoxycarbonylaminophenyl)-3(2H)-pyridazinone, 4,5-dihydro-6-(p-methoxycarbonylaminophenyl)-5-methyl-3(2H)-pyridazinone, 4,5-dihydro-6-(p-ethoxycarbonylaminophenyl)-3(2H)-pyridazinone, 4,5-dihydro-6-(p-ethoxycarbonylaminophenyl)-5-methyl-3(2H)-pyridazinone, 4,5-dihydro-6-(p-propoxycarbonylaminophenyl)-3(2H)-pyridazinone, 4,5-dihydro-5-methyl-6-(p-propoxycarbonylaminophenyl)-3(2H)-pyridazinone, 4,5-dihydro-6-(p-isopropoxycarbonylaminophenyl)-3(2H)-pyridazinone, 4,5-dihydro-6-(p-isopropoxycarbonylaminophenyl)-5-methyl-3(2H)-pyridazinone, 6-(p-butoxycarbonylaminophenyl)-4,5-dihydro-3(2H)-pyridazinone, 6-(p-butoxycarbonylaminophenyl)-4,5-dihydro-5-methyl-3(2H)-pyridazinone, 4,5-dihydro-6-(p-isobutoxycarbonylaminophenyl)-5-methyl-3(2H)-pyridazinone, 6-[p-(sec.-butoxy)-carbonylaminophenyl]-4,5-dihydro-5-methyl-3(2H)-pyridazinone, 6-[p-(tert.-butoxy)-carbonylaminophenyl]-4,5-dihydro-5-methyl-3(2H)-pyridazinone, 6-(p-chloromethoxycarbonylaminophenyl)-4,5-dihydro-3(2H)-pyridazinone, 6-(p-chloromethoxycarbonylaminophenyl)-4,5-dihydro-5-methyl-3(2H)-pyridazinone, 6-(p-dichloromethoxycarbonylaminophenyl)-4,5-dihydro-3(2H)-pyridazinone, 6-(p-dichloromethoxycarbonylaminophenyl)-4,5-dihydro-5-methyl-3(2H)-pyridazinone, 4,5-dihydro-6-(p-trifluoromethoxycarbonylaminophenyl)-3(2H)-pyridazinone, 4,5-dihydro-5-methyl-6-(p-trifluoromethoxycarbonylaminophenyl)-3(2H)-pyridazinone, 6-[p-(1-chloroethoxycarbonylamino)-phenyl]-4,5-dihydro-3(2H)-pyridazinone, 6-[p-(1-chloroethoxycarbonylamino)-phenyl]-4,5-dihydro-5-methyl-3(2H)-pyridazinone, 6-[p-(2-chloroethoxycarbonylamino)-phenyl]-4,5-dihydro-3(2H)-pyridazinone, 6-[p-(2-chloroethoxycarbonylamino)-phenyl]-4,5-dihydro-5-methyl-3(2H)-pyridazinone, 6-[p-(2-bromoethoxycarbonylamino)-phenyl]-4,5-dihydro-3(2H)-pyridazinone, 6-[p-(2-bromoethoxycarbonylamino)-phenyl]-4,5-dihydro-5-methyl-3(2H)-pyridazinone, 4,5-dihydro-6-[p-(2-fluoroethoxycarbonylamino)-phenyl]-3(2H)-pyridazinone, 4,5-dihydro-6-[p-(2-fluoroethoxycarbonylamino)-phenyl]-5-methyl-3(2H)-pyridazinone, 6-[p-(1,2-dichloroethoxycarbonylamino)-phenyl]-4,5-dihydro-3(2H)-pyridazinone, 6-[p-(1,2-dichloroethoxycarbonylamino)-phenyl]-4,5-dihydro-5-methyl-3(2H)-pyridazinone, 4,5-dihydro-5-methyl-6-[p-(1,1,2-trichloroethoxycarbonylamino)-phenyl]-3(2H)-pyridazinone, 4,5-dihydro-5-methyl-6-[p-(2,2,2-trichloroethoxycarbonylamino)-phenyl]-3(2H)-pyridazinone, 4,5-dihydro-6-[p-(2,2,2-trifluoroethoxycarbonylamino)-phenyl]-3(2H)-pyridazinone, 4,5-dihydro-5-methyl-6-[p-(2,2,2-trifluoroethoxycarbonylamino)-phenyl]-3(2H)-pyridazinone, 6-[p-(2-bromopropoxycarbonylamino)-phenyl]-4,5-dihydro-5-methyl-3(2H)-pyridazinone, 6-[p-3-chloropropoxycarbonylamino)-phenyl]-4,5-dihydro-5-methyl-3(2H)-pyridazinone, 6-[p-(2,3-dichloropropoxycarbonylamino)-phenyl]-4,5-dihydro-5-methyl-3(2H)-pyridazinone, 6-[p-(2-chloroisopropoxycarbonylamino)-phenyl]-4,5-dihydro-3(2H)-pyridazinone, 6-[p-(2-chloroisopropoxycarbonylamino)-phenyl]-4,5-dihydro-5-methyl-3(2H)-pyridazinone, 6-[p-(2,2'-dichloroisopropoxycarbonylamino)-phenyl]-4,5-dihydro-5-methyl-3(2H)-pyridazinone, 6-[p-(2-chlorobutoxycarbonylamino)-phenyl]-4,5-dihydro-3(2H)-pyridazinone, 6-[p-(2-chlorobutoxycarbonylamino)-phenyl]-4,5-dihydro-5-methyl-3(2H)-pyridazinone, 6-[p-(1-chloromethylpropoxycarbonylamino)-phenyl]-4,5-dihydro-3(2H)-pyridazinone, 6-[p-(1-chloromethylpropoxycarbonylamino)-phenyl]-4,5-dihydro-5-methyl-3(2)-pyridazinone, 6-[p-(2-chloroisobutoxycarbonylamino)-phenyl]-4,5-dihydro-5-methyl-3(2H)-pyridazinone, 4,5-dihydro-6-[p-(2-methoxyethoxycarbonylamino)-phenyl]-3(2H)-pyridazinone, 4,5-dihydro-6-[p-(2-methoxyethoxycarbonylamino)-phenyl]-5-methyl-3(2H)-pyridazinone, 4,5-dihydro-6-[p-(2-ethoxyethoxycarbonylamino)-phenyl]-5-methyl-3(2H)-pyridazinone, 4,5-dihydro-6-[p-(2-methoxypropoxycarbonylamino)-phenyl]-5-methyl-3(2H)-pyridazinone, 4,5-dihydro-6-[p-(3-methoxypropoxycarbonylamino)-phenyl]-5-methyl-3(2H)-pyridazinone, 4,5-dihydro-6-[p-(3-ethoxypropoxycarbonylamino)-phenyl]-5-methyl-3(2H)-pyridazinone, 4,5-dihydro-6-[p-(2-methoxyisopropoxycarbonylamino)-phenyl]-5-methyl-3(2H)-pyridazinone, 6-(p-cyclopropylmethoxycarbonylaminophenyl)-4,5-dihydro-3(2H)-pyridazinone, 6-(p-cyclopropylmethoxycarbonylaminophenyl)-4,5-dihydro-5-methyl-3(2H)-pyridazinone, 4,5-dihydro-6-[p-(1-methylcyclopropylmethoxycarbonylamino)-phenyl]-3(2H)-pyridazinone, 4,5-dihydro-5-methyl-6-[p-(1-methylcyclopropylmethoxycarbonylamino)-phenyl]-3(2H)-pyridazinone, 4,5-dihydro-6-[p-(2-methylcyclopropylmethoxycarbonylamino)-phenyl]-3(2H)-pyridazinone, 4,5-dihydro-5-methyl-6-[p-(2-methylcyclopropylmethoxycarbonylamino)-phenyl]-3(2H)-pyridazinone, 6-(p-cyclobutylmethoxycarbonylaminophenyl)-4,5-dihydro-3(2H)-pyridazinone, 6-(p-cyclobutylmethoxycarbonylaminophenyl)-4,5-dihydro-5-methyl-3(2H)-pyridazinone, 6-(p-cyclopentylmethoxycarbonylaminophenyl)-4,5-dihydro-5-methyl-3(2H)-pyridazinone, 6-(p-cyclohexylmethoxycarbonylaminophenyl)-4,5-dihydro-5-methyl-3(2H)-pyridazinone, 6-[p-(1-cyclopropylethoxycarbonylamino)-phenyl]-4,5-dihydro-3(2H)-pyridazinone, 6-[p-(1-cyclopropylethoxycarbonylamino)-phenyl]-4,5-dihydro-5-methyl-3(2H)-pyridazinone, 6-[p-(1-cyclobutylethoxycarbonylamino)-phenyl]-4,5-dihydro-5-methyl-3(2H)-pyridazinone, 6-[p-(2-cyclopropylethoxycarbonylamino)-phenyl]-4,5-dihydro-3(2H)-pyridazinone, 6-[p-(2-cyclopropylethoxycarbonylamino)-phenyl]-4,5-dihydro-5-methyl-3(2H)-pyridazinone, 6-[p-(2-cyclobutylethoxycarbonylamino)-phenyl]-4,5-dihydro-5-methyl-3(2H)-pyridazinone, 6-[p-(1-cyclopropylpropoxycarbonylamino)-phenyl]-4,5-dihydro-5-methyl-3(2H)-pyridazinone, 6-[p-(2-cyclobutylpropoxycarbonylamino)-phenyl]-4,5-dihydro-5-methyl-3(2H)-pyridazinone, 6-(p-benzyloxycarbonylaminophenyl)-4,5-dihydro-3(2H)-pyridazinone, 6-(p-benzyloxycarbonylaminophenyl)-4,5-dihydro-5-methyl-3(2H)-pyridazinone, 4,5-dihydro-6-[p-(1-phenylethoxycarbonylamino)-phenyl]-3(2H)-pyridazinone, 4,5-dihydro-5-methyl-6-[p-(1-phenylethoxycarbonylamino)-phenyl]-3(2H)-pyridazinone, 4,5-dihydro-5-methyl-6-[p-(2-phenylethoxycarbonylamino)-phenyl]-3(2H)-pyridazinone, 4,5-dihydro-5-methyl-6-[p-(1-phenylpropoxycarbonylamino)-phenyl]-3(2H)-pyridazinone, 4,5-dihydro-5-methyl-6-[p-(2-phenylpropoxycarbonylamino)-phenyl]-3(2H)-pyridazinone, 4,5-dihydro-5-methyl-6-[p-(1-methyl-2-phenylethoxycarbonylamino)-phenyl]-3(2H)-pyridazinone, 4,5-dihydro-5-methyl-6-[p-(p-methylbenzyloxycarbonylamino)-phenyl]-3(2H)-pyridazinone, 4,5-dihydro-6-[p-(m-methoxybenzyloxycarbonylamino)-phenyl]-5-methyl-3(2H)-pyridazinone, 4,5-dihydro-6-[p-(m,p-dimethoxybenzyloxycarbonylamino)-phenyl]-5-methyl-3(2H)-pyridazinone, 6-[p-(o-chlorobenzyloxycarbonylamino)-phenyl]-4,5-dihydro-5-methyl-3(2H)-pyridazinone, 6-[p-(m-chlorobenzyloxycarbonylamino)-phenyl]-4,5-dihydro-5-methyl-3(2H)-pyridazinone, 6-[p-(p-chlorobenzyloxycarbonylamino)-phenyl]-4,5-dihydro-5-methyl-3(2H)-pyridazinone, 4,5-dihydro-6-[p-(p-fluorobenzyloxycarbonylamino)-phenyl]-5-methyl-3(2H)-pyridazinone, 4,5-dihydro-5-methyl-6-[p-(m-trifluoromethylbenzyloxycarbonylamino)-phenyl]-3(2H)-pyridazinone, 4,5-dihydro-5-methyl-6-[p-(p-nitrobenzyloxycarbonylamino)-phenyl]-3(2H)-pyridazinone, 4,5-dihydro-6-[p-[2-(m,p-dimethoxyphenyl)-ethoxycarbonylamino]-phenyl]-5-methyl-3(2H)-pyridazinone, 6-(p-cyclopropoxycarbonylaminophenyl)-4,5-dihydro-3(2H)-pyridazinone, 6-(p-cyclopropoxycarbonylaminophenyl)-4,5-dihydro-5-methyl-3-(2H)-pyridazinone, 4,5-dihydro-6-[p-(1-methylcyclopropoxycarbonylamino)-phenyl]-3(2H)-pyridazinone, 4,5-dihydro-5-methyl-6-[p-(1-methylcyclopropoxycarbonylamino)-phenyl]-3(2H)-pyridazinone, 4,5-dihydro-6-[p-(2-methylcyclopropoxycarbonylamino)-phenyl]-3(2H)-pyridazinone, 4,5-dihydro-5-methyl-6-[p-(2-methylcyclopropoxycarbonylamino)-phenyl]-3(2H)-pyridazinone, 4,5-dihydro-6-[p-(2,2-dimethylcyclopropoxycarbonylamino)-phenyl]-5-methyl-3(2H)-pyridazinone, 6-(p-cyclobutoxycarbonylaminophenyl)-4,5-dihydro-3(2H)-pyridazinone, 6-(p-cyclobutoxycarbonylaminophenyl)-4,5-dihydro-5-methyl-3(2H)-pyridazinone, 4,5-dihydro-5-methyl-6-[p-(1-methylcyclobutoxycarbonylamino)-phenyl]-3(2H)-pyridazinone, 4,5-dihydro-5-methyl-6-[p-(2-methylcyclobutoxycarbonylamino)-phenyl]-3(2H)-pyridazinone, 4,5-dihydro-5-methyl-6-[p-(3-methylcyclobutoxycarbonylamino)-phenyl]-3(2H)-pyridazinone, 4,5-dihydro-6-[p-(2,2-dimethylcyclobutoxycarbonylamino)-phenyl]-5-methyl-3(2H)-pyridazinone, 4,5-dihydro-6-[p-(3,3-dimethylcyclobutoxycarbonylamino)-phenyl]-5-methyl-3(2H)-pyridazinone, 6-(p-cyclopentoxycarbonylaminophenyl)-4,5-dihydro-5-methyl-3(2H)-pyridazinone, 6-(p-cyclohexoxycarbonylaminophenyl)-4,5-dihydro-5-methyl-3-(2H)-pyridazinone, 6-(p-allyloxycarbonylaminophenyl)-4,5-dihydro-3(2H)-pyridazinone, 6-(p-allyloxycarbonylaminophenyl)-4,5-dihydro-5-methyl-3(2H)-pyridazinone, 6-[p-(but-2-enyloxycarbonylamino)-phenyl]-4,5-dihydro-5-methyl-3(2H)-pyridazinone, 6-[p-(but-3-enyloxycarbonylamino)-phenyl]-4,5-dihydro-5-methyl-3(2H)-pyridazinone, 4,5-dihydro-5-methyl-6-[p-(1-methylallyloxycarbonylamino)-phenyl]-3(2H)-pyridazinone, 4,5-dihydro-5-methyl-6-[p-(2-methylallyloxycarbonylamino)-phenyl]-3(2H)-pyridazinone, 4,5-dihydro-6-[p-(prop-2-ynyloxycarbonylamino)-phenyl]-3(2H)-pyridazinone, 4,5-dihydro-5-methyl-6-[p-(prop-2-ynyloxycarbonylamino)-phenyl]-3(2H)-pyridazinone, 6-[p-(but-2-ynyloxycarbonylamino)-phenyl]-4,5-dihydro-3(2H)-pyridazinone, 6-[p-(but-2-ynyloxycarbonylamino)-phenyl]-4,5-dihydro-5-methyl-3(2H)-pyridazinone, 6-[p-(but-3-ynyloxycarbonylamino)-phenyl]-4,5-dihydro-3(2H)-pyridazinone, 6-[p-(but-3-ynyloxycarbonylamino)-phenyl]-4,5-dihydro-5-methyl-3(2H)-pyridazinone, 4,5-dihydro-6-[p-(1-methylprop-2-ynyloxycarbonylamino)-phenyl]-3(2H)-pyridazinone, 4,5-dihydro-5-methyl-6-[p-(1-methylprop-2-ynyloxycarbonylamino)-phenyl]-3(2H)-pyridazinone, 4,5-dihydro-5-methyl-6-[p-(pent-2-ynyloxycarbonylamino)-phenyl]-3(2H)-pyridazinone, 4,5-dihydro-6-[p-(1,1-dimethylprop-2-ynyloxycarbonylamino)-phenyl]-5-methyl-3(2H)-pyridazinone, 4,5-dihydro-6-(p-phenoxycarbonylaminophenyl)-3(2H)-pyridazinone, 4,5-dihydro-5-methyl-6-(p-phenoxycarbonylaminophenyl)-3(2H)-pyridazinone, 4,5-dihydro-5-methyl-6-[p-(m-tolyloxycarbonylamino)-phenyl]-3(2H)-pyridazinone, 4,5-dihydro-6-[p-(o-methoxyphenoxycarbonylamino)-phenyl]-5-methyl-3(2H)-pyridazinone, 4,5-dihydro-6-[p-(m-methoxyphenoxycarbonylamino)-phenyl]-5-methyl-3(2H)-pyridazinone, 6-[p-(o-chlorophenoxycarbonylamino)-phenyl]-4,5-dihydro-5-methyl-3(2H)-pyridazinone, 6-[p-(m-chlorophenoxycarbonylamino)-phenyl]-4,5-dihydro-5-methyl-3(2H)-pyridazinone, 6-[p-(p-chlorophenoxycarbonylamino)-phenyl]-4,5-dihydro-5-methyl-3(2H)-pyridazinone, 4,5-dihydro-6-[p-(p-fluorophenoxycarbonylamino)-phenyl]-5-methyl-3(2H)-pyridazinone, 4,5-dihydro-5-methyl-6-[p-(m-trifluoromethylphenoxycarbonylamino)-phenyl]-3(2H)-pyridazinone, 6-[p-(p-cyanophenoxycarbonylamino)-phenyl]-4,5-dihydro-5-methyl-3(2H)-pyridazinone, 4,5-dihydro-5-methyl-6-[p-(o-nitrophenoxycarbonylamino)-phenyl]-3(2H)-pyridazinone, 4,5-dihydro-5-methyl-6-[p-(p-nitrophenoxycarbonylamino)-phenyl]-3(2H)-pyridazinone, 4,5-dihydro-6-(p-methylmercaptocarbonylaminophenyl)-3(2H)-pyridazinone, 4,5-dihydro-5-methyl-6-(p-methylmercaptocarbonylaminophenyl)-3(2H)-pyridazinone, 4,5-dihydro-6-(p-ethylmercaptocarbonylaminophenyl)-3(2H)-pyridazinone, 4,5-dihydro-6-(p-ethylmercaptocarbonylaminophenyl)-5-methyl-3(2H)-pyridazinone, 4,5-dihydro-6-(p-propylmercaptocarbonylaminophenyl)-3(2H)-pyridazinone, 4,5-dihydro-5-methyl-6-(p-propylmercaptocarbonylaminophenyl)-3(2H)-pyridazinone, 4,5-dihydro-6-(p-isopropylmercaptocarbonylaminophenyl)-3(2H)-pyridazinone, 4,5-dihydro-6-(p-isopropylmercaptocarbonylaminophenyl)-5-methyl-3(2H)-pyridazinone, 6-(p-butylmercaptocarbonylaminophenyl)-4,5-dihydro-5-methyl-3(2H)-pyridazinone, 4,5-dihydro-6-(p-trifluoromethylmercaptocarbonylaminophenyl)-3(2H)-pyridazinone, 4,5-dihydro-5-methyl-6-(p-trifluoromethylmercaptocarbonylaminophenyl)-3(2H)-pyridazinone, 6-[p-(2-chloroethylmercaptocarbonylamino)-phenyl]-4,5-dihydro-3(2H)-pyridazinone, 6-[p-(2-chloroethylmercaptocarbonylamino)-phenyl]-4,5-dihydro-5-methyl-3(2H)-pyridazinone, 6-[p-(2-bromoethylmercaptocarbonylamino)-phenyl]-4,5-dihydro-5-methyl-3(2H)-pyridazinone, 4,5-dihydro-6-[p-(2-fluoroethylmercaptocarbonylamino)-phenyl]-5-methyl-3(2H)-pyridazinone, 4,5-dihydro-6-[p-(2,2,2-trifluoroethylmercaptocarbonylamino)-phenyl]-3(2H)-pyridazinone, 4,5-dihydro-5-methyl-6-[p-(2,2,2-trifluoroethylmercaptocarbonylamino)-phenyl]-3(2H)-pyridazinone, 6-[p-(3-chloropropylmercaptocarbonylamino)-phenyl]-4,5-dihydro-5-methyl-3(2H)-pyridazinone, 6-[p-(2,3-dichloropropylmercaptocarbonylamino)-phenyl]-4,5-dihydro-5-methyl-3(2H)-pyridazinone, 4,5-dihydro-6-[p-(2-methoxyethylmercaptocarbonylamino)-phenyl]-5-methyl-3(2H)-pyridazinone, 4,5-dihydro-6-[p-(2-ethoxyethylmercaptocarbonylamino)-phenyl]-5-methyl-3(2H)-pyridazinone, 6-(p-cyclopropylmethylmercaptocarbonylaminophenyl)-4,5-dihydro-3(2H)-pyridazinone, 6-(p-cyclopropylmethylmercaptocarbonylaminophenyl)-4,5-dihydro-5-methyl-3(2H)-pyridazinone, 6-(p-cyclobutylmethylmercaptocarbonylaminophenyl)-4,5-dihydro-5-methyl-3(2H)-pyridazinone, 6-(p-cyclopentylmethylmercaptocarbonylaminophenyl)-4,5-dihydro-5-methyl-3(2H)-pyridazinone, 6-(p-benzylmercaptocarbonylaminophenyl)-4,5-dihydro-3(2H)-pyridazinone, 6-(p-benzylmercaptocarbonylaminophenyl)-4,5-dihydro-5-methyl-3(2H)-pyridazinone, 4,5-dihydro-5-methyl-6-[p-(1-phenylethylmercaptocarbonylamino)-phenyl]-3(2H)-pyridazinone, 4,5-dihydro-5-methyl-6-[p-(2-phenylethylmercaptocarbonylamino)-phenyl]-3(2H)-pyridazinone, 4,5-dihydro-5-methyl-6-[p-(p-methylbenzylmercaptocarbonylamino)-phenyl]-3(2H)-pyridazinone, 4,5-dihydro-6-[p-(p-methoxybenzylmercaptocarbonylamino)-phenyl]-5-methyl-3(2H)-pyridazinone, 6-[p-(p-chlorobenzylmercaptocarbonylamino)-phenyl]-4,5-dihydro-5-methyl-3(2H)-pyridazinone, 4,5-dihydro-6-[p-(p-fluorobenzylmercaptocarbonylamino)phenyl]-5-methyl-3(2H)-pyridazinone, 4,5-dihydro-5-methyl-6[p-(m-trifluoromethylbenzylmercaptocarbonylamino)-phenyl]-3(2H)-pyridazinone, 4,5-dihydro-5-methyl-6-[p-(p-nitrobenzylmercaptocarbonylamino)-phenyl]-3(2H)-pyridazinone, 6-(p-cyclopropylmercaptocarbonylaminophenyl)-4,5-dihydro-3(2H)-pyridazinone, 6-(p-cyclopropylmercaptocarbonylaminophenyl)-4,5-dihydro-5-methyl-3(2H)-pyridazinone, 6-(p-cyclobutylmercaptocarbonylaminophenyl)-4,5-dihydro-5-methyl-3(2H)-pyridazinone, 6-(p-cyclohexylmercaptocarbonylaminophenyl)-4,5-dihydro-5-methyl-3(2H)-pyridazinone, 6-(p-allylmercaptocarbonylaminophenyl)-4,5-dihydro-3(2H)-pyridazinone, 6-(p-allylmercaptocarbonylaminophenyl)-4,5-dihydro-5-methyl-3(2H)-pyridazinone, 6-[p-(but-2-enylmercaptocarbonylamino)-phenyl]-4,5-dihydro-5-methyl-3(2H)-pyridazinone, 6-[p-(but-3-enylmercaptocarbonylamino)-phenyl]-4,5-dihydro-5-methyl-3(2H)-pyridazinone, 4,5-dihydro-6-[p-(prop-2-ynylmercaptocarbonylamino)-phenyl]-3(2H)-pyridazinone, 4,5-dihydro-5-methyl-6-[p-(prop-2-ynylmercaptocarbonylamino)-phenyl]-3(2H)-pyridazinone, 4,5-dihydro-5-methyl-6-(p-phenylmercaptocarbonylaminophenyl)-3(2H)-pyridazinone, 4,5-dihydro-5-methyl-6-[p-(p-tolylmercaptocarbonylamino)-phenyl]-3(2H)-pyridazinone, 4,5-dihydro-6-[p-(o-methoxyphenylmercaptocarbonylamino)-phenyl]-5-methyl-3(2H)-pyridazinone, 6-[p-(p-chlorophenylmercaptocarbonylamino)-phenyl]-4,5-dihydro-5-methyl-3(2H)-pyridazinone, 4,5-dihydro-6-[p-(p-fluorophenylmercaptocarbonylamino)-phenyl]-5-methyl-3(2H)-pyridazinone, 4,5-dihydro-5-methyl-6-[p-(m-trifluoromethylphenylmercaptocarbonylamino)-phenyl]-3(2H)-pyridazinone, 6-[p-(p-cyanophenylmercaptocarbonylamino)-phenyl]-4,5-dihydro-5-methyl3(2H)-pyridazinone and 4,5-dihydro-5-methyl-6-[p-(p-nitrophenylmercaptocarbonylamino)-phenyl]-3(2H)-pyridazinone.

It is to be noted that the compounds of the formula I, where $R^1$ is not hydrogen, have an asymmetrical carbon atom in the 5-position and are obtained as racemates. The present invention also encompasses the enantiomers. If a separation is desired, it is advantageously carried out at the stage of a compound of the formula II, using conventional methods, for example the formation of diastereomeric salts with optically active auxiliary acids, such as dibenzoyltartaric acid or camphor-10-sulfonic acid.

Where $R^2$ has a suitable meaning, for example 2-methylcyclopropyl, the compounds of the formula I furthermore exhibit geometrical cis-trans isomerism. The present invention encompasses the cis- and trans-isomers and their mixtures.

The novel dihydropyridazinones of the formula I exhibit thrombocyte aggregation-inhibiting and blood pressure-lowering properties. They are useful as antihypertensives and for the prophylaxis and therapy of thrombo-embolic disorders.

The advantage thrombocyte aggregationinhibiting action can be shown by comparison with acetylsalicyclic acid, for example by experiments on collagen-induced aggregation of human thrombocytes. The blood pressure-lowering action can be demonstrated, for example, on rats under urethane narcosis. The reference substance can be, for example, dihydralazine.

Specifically, the following methods were used to investigate the pharmacodynamic properties.

1. Inhibition of collagen-induced aggregation of rat thrombocytes ex vivo.

The substances are administered orally to groups of 10–15 male Sprague-Dawley rats (200–250 g). 1 hour after administration, blood is taken under ether narcosis and thrombocyte-rich plasma is isolated by centrifuging (300 g, 10 minutes at 4° C.). The thrombocyte aggregation is measured photometrically, with addition of magnesium chloride (final concentration 10 millimoles/l) and of Collagen Stago (final concentration 0.02 mg/ml), in a Born Aggregometer Mk 3. The maximum change in extinction per second is used as the measure of the aggregation.

The ED 33% is determined as the dose which inhibits the collagen-induced thrombocyte aggregation by 33%.

2. Anti-hypertensive action on spontaneously hypertonic rats.

The substances are administered orally to male, spontaneously hypertonic, Okamoto rats (4–8 animals per dose; weight 270–360 g). The systolic blood pressure is measured non-surgically, before and 2 hours after administration, on the tails of the rats, by means of piezoelectric recorders.

The ED 20% is determined as the dose which lowers the systolic pressure by 20%, with due account taken of the values found on untreated control animals.

The results obtained are shown in Table 1 below, in respect of which the following should be noted:

The recognized agents acetylsalicyclic acid (ASA) and dihydralazine are used as comparative substances, having a relative activity (R.A.) of 1. Comparison is also made with a structurally similar compound of the prior art, namely 6-[p-(2-chloropropionylamino)-phenyl]-4,5-dihydro-5-methyl-3(2H)-pyridazinone (compound $V_1$), which has already been shown to be very active.

The numerical data obtained show that all the novel compounds listed in the Table are substantially more effective than the commercial compounds in respect of at least one of the effects investigated.

TABLE 1

| Compound of Example No. | Inhibition of thrombocyte aggregation | | Anti-hypertensive effect | |
| --- | --- | --- | --- | --- |
| | ED 33% | R.A. | ED 20% | R.A. |
| 2 | 0.532 | 437.97 | 0.793 | 8.64 |
| 6 | 1.16 | 200.86 | 0.285 | 24.03 |
| 7 | 2.97 | 78.45 | 0.382 | 17.93 |
| 12 | 0.140 | 1,664.29 | 1.0 | 6.85 |
| 18 | 0.182 | 1,280.23 | 0.548 | 12.5 |
| 28 | 0.850 | 274.12 | 2.15 | 3.19 |
| 40 | 13.8 | 16.88 | 0.265 | 25.85 |
| $V_1$ | 0.82 | 284.15 | 1.16 | 5.91 |
| ASA | 233 | 1.00 | — | — |
| Dihydralazine | — | — | 6.85 | 1.00 |

Accordingly, the present invention also relates to therapeutic agents or formulations which contain a compound of the formula I as the active compound, together with conventional pharmaceutical carriers and diluents, and to the use of these compounds for therapeutic purposes, especially in the treatment of high blood pressure and of thrombo-embolic disorders.

The therapeutic agents or formulations are prepared in a known manner, using the conventional carriers or diluents, the conventional pharmaceutical auxiliaries, and a suitable dose of the active compound, in accordance with the desired route of administration. Appropriate doses for man are from 1 to 100 mg, preferably from 5 to 50 mg, oral administration being preferred.

Examples of forms suitable for oral administration are tablets, film tablets, dragees, capsules, pills, powders, solutions, suspensions and depot forms.

For practical use, the compounds to be employed according to the invention are compounded with the conventional pharmaceutical carriers. For example, appropriate tablets can be obtained by mixing the active compound with conventional auxiliaries, for example inert diluents, such as dextrose, sugar, sorbitol, polyvinylpyrrolidone, mannitol, calcium carbonate, calcium phosphate or lactose, disintegrating agents, such as corn starch, alginic acid or polyvinylpyrrolidone, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers (cf. L. G. Godman and A. Gilman, The Pharmacological Basis of Therapeutics).

Correspondingly, dragees can be prepared from cores, prepared similarly to the tablets, and coatings containing the conventional agents, for example polyvinylpyrrolidone or shellac, gum arabic, talc, titanium dioxide or sugar. The dragee coating can also consist of several layers, and the auxiliaries mentioned above in connection with tablets can be used.

The Examples which follow illustrate the preparation of the novel 6-aryl-4,5-dihydro-3(2H)-pyridazinones.

EXAMPLE 1

6.0 g (31.7 millimoles) of 6-(p-aminophenyl)-4,5-dihydro-3(2H)-pyridazinone and 3.3 g (34.9 millimoles) of methyl chloroformate in 100 ml of absolute toluene are kept for 6 hours at 80° C. The product is filtered off at 10° C., washed first with toluene and then with water, and recrystallized from dimethylformamide/water. 3.3 g (42% of theory) of 4,5-dihydro-6-(p-methoxycarbonylaminophenyl)-3(2H)-pyridazinone are obtained as beige crystals, of melting point 246°–247° C. (with decomposition).

Analysis for $C_{12}H_{13}N_3O_3$: Calculated: C 58.3 H 5.3 N 17.0%. Found: C 58.1 H 5.3 N 16.8%.

EXAMPLE 2

6.0 g (29.5 millimoles) of 6-(p-aminophenyl)-4,5-dihydro-dihydro-5-methyl-3(2H)-pyridazinone and 3.3 g (34.9 millimoles) of methyl chloroformate in 100 ml of absolute toluene are kept for 6 hours at 80° C. The product is filtered off at 10° C., washed first with toluene and then with water, and recrystallized from dimethylformamide/water. 3.1 g (40% of theory) of 4,5-dihydro-6-(p-methoxycarbonylaminophenyl)-5-methyl-3(2H)-pyridazinone are obtained as colorless crystals, of melting point 228°–229° C.

Analysis for $C_{15}H_{15}N_3O_3$: Calculated: C 59.8 H 5.8 N 16.1%. Found: C 59.8 H 5.7 N 16.3%.

EXAMPLE 3

(a) 10.0 g (51.8 millimoles) of 3-(p-aminobenzoyl)propionic acid, 6.7 g (61.7 millimoles) of ethyl chloroformate and 100 ml of absolute tetrahydrofuran are refluxed for 10 hours. The product is filtered off at 10° C., washed with water and recrystallized from dimethylformamide/water. 7.8 g (57% of theory) of 3-(p-ethoxycarbonylaminobenzoyl)-propionic acid are obtained as pale beige crystals, of melting point 206°–207° C.

Analysis for $C_{13}H_{15}NO_5$: Calculated: C 58.9 H 5.7 N 5.3%. Found: C 58.7 H 5.7 N 5.3%.

(b) 3.5 g (13.2 millimoles) of 3-(p-ethoxycarbonylaminobenzoyl)-propionic acid, 0.66 g (13.2 millimoles) of hydrazine hydrate and 50 ml of ethanol are refluxed for 7 hours. The product is filtered off at 10° C. and dried under reduced pressure at 50° C., giving 3.2 g (93% of theory) of 4,5-dihydro-6-(p-ethoxycarbonylaminophenyl)-3(2H)-pyridazinones as colorless crystals, of melting point 242°–243° C.

Analysis for $C_{13}H_{15}N_3O_3$: Calculated: C 59.8 H 5.8 N 16.1%. Found: C 59.6 H 5.9 N 16.1%

EXAMPLE 4

(a) 75 ml of absolute ethanol are added, with stirring, to 11.0 g (44.5 millimoles) of ethyl 3-(p-isocyanatobenzyl) propionate (German Laid-Open Application No. DOS 2,157,453). The reaction mixture is then stirred for 2 hours at room temperature. The product is filtered off at 10° C. and dried under reduced pressure at 50° C., giving 11.4 g (87% of theory) of ethyl 3-(p-ethoxycarbonylaminobenzoyl) propionate as colorless crystals, of melting point 151°–152° C.

Analysis for $C_{15}H_{19}NO_5$: Calculated: C 61.4 H 6.5 N 4.8%. Found: C 61.5 H 6.3 4.9%.

(b) 2.0 g (6.8 millimoles) of ethyl 3-(p-ethoxycarbonylaminobenzoyl) propionate, 0.34 g (6.8 millimoles) of hydrazine hydrate and 20 ml of ethanol are refluxed for 6 hours. The product is filtered off at 10° C. and dried under reduced pressure at 50° C., giving 1.1 g (62% of theory) of 4,5-dihydro-6-(p-ethoxycarbonylaminophenyl)-3(2H)-pyridazinone as colorless crystals, identical with the compound from Example 3b.

EXAMPLE 5

Example 1 is repeated using ethyl chloroformate (3.8 g (35.0 millimoles) instead of methyl chloroformate. After recrystallizing the product from dimethylformamide/water, 3.7 g (45% of theory) of 4,5-dihydro-6-(p-ethoxycarbonylaminophenyl)-3(2H)-pyridazinone are obtained as almost colorless crystals, identical with the compound from Example 3b.

EXAMPLE 6

Example 2 is repeated, using ethyl chloroformate (3.8 g (35.0 millimoles)) in place of methyl chloroformate. After recrystallizing the product from dimethylformamide/water, 3.5 g (43% of theory) of 4,5-dihydro-6-(p-ethoxycarbonylaminophenyl)-5-methyl-3(2H)-pyridazinone are obtained as colorless crystals, of melting point 219°–221° C.

Analysis for $C_{14}H_{17}N_3O_3$: Calculated: C 61.1 H 6.2 N 15.3%. Found: C 61.0 H 6.3 N 15.5%.

EXAMPLE 7

Example 2 is repeated with propyl chloroformate (5.45 g (44.5 millimoles) in place of methyl chloroformate. After recrystallizing the product from dimethylformamide/water, 3.5 g (41% of theory) of 4,5-dihydro-5-methyl-6-(p-propoxycarbonylaminophenyl)-3(2H)-pyridazinone are obtained as pale yellow crystals, of melting point 207°–208° C.

Analysis for $C_{15}H_{19}N_3O_3$: Calculated: C 62.3 H 6.6 N 14.5%. Found: C 62.6 H 6.4 N 14.8%.

EXAMPLE 8

6.0 g (29.5 millimoles) of 6-(p-aminophenyl)-4,5-dihydro-5-methyl-3(2H)-pyridazinone, 4.0 g (32.6 millimoles) of isopropyl chloroformate and 100 ml of absolute toluene are refluxed for 16 hours. The product is filtered off at 10° C., washed first with toluene and then with water, and recrystallized twice from dimethylformamide/water. 4.3 g (50% of theory) of 4,5-dihydro-6-(p-isopropoxycarbonylaminophenyl)-5-methyl-3(2H)-pyridazinone are obtained as colorless crystals, of melting point 236°–237° C.

Analysis for $C_{15}H_{19}N_3O_3$: Calculated: C 62.3 H 6.6 N 14.5%. Found: C 62.3 H 6.7 N 14.8%.

EXAMPLE 9

Example 2 is repeated, using butyl chloroformate (4.45 g (32.6 millimoles)) in place of methyl chloroformate. After recrystallizing the product twice from ethanol/water, 3.0 g (33% of theory) of 6-(p-butoxycarbonylaminophenyl)-4,5-dihydro-5-methyl-3(2H)-pyridazinone are obtained as colorless crystals, of melting point 203°–204° C.

Analysis for $C_{16}H_{21}N_3O_3$: Calculated: C 63.3 H 7.0 N 13.9%. Found: C 63.0 H 6.9 N 14.0%.

EXAMPLE 10

Example 2 is repeated, using isobutyl chloroformate (4.45 g (32.6 millimoles)) in place of methyl chloroformate. After recrystallizing the product from ethanol/water, 3.6 g (40% of theory) of 4,5-dihydro-6-(p-isobutoxycarbonylaminophenyl)-5-methyl-3(2H)- pyridazinone are obtained as colorless crystals of melting point 186°–187° C.

Analysis for $C_{16}H_{21}N_3O_3$: Calculated: C 63.3 H 7.0 N 13.9%. Found: C 63.5 H 6.8 N 14.1%.

EXAMPLE 11

Example 1 is repeated, using 2-chloroethyl chloroformate (5.4 g (37.8 millimoles)) in place of methyl chloroformate. After twice recrystallizing the product from ethanol/water, 3.9 g (42% of theory) of 6-[p-(2-chloroethoxycarbonylamino)-phenyl]-4,5-dihydro3(2H)-pyridazinone are obtained as colorless crystals of melting point 232°–233° C.

Analysis for $C_{13}H_{14}ClN_3O_3$: Calculated: C 52.8 H 4.8 Cl 12.0 N 14.2%. Found: C 53.0 H 4.9 Cl 11.8 N 14.4%.

EXAMPLE 12

Example 2 is repeated, using 2-chloroethyl chloroformate (4.65 g (32.5 millimoles)) in place of methyl chloroformate. After recrystallizing the product from ethanol/water, 3.6 g (39% of theory) of 6-[p-(2-chloroethoxycarbonylamino)-phenyl]-4,5-dihydro-5-methyl-3(2H)-pyridazinone are obtained as almost colorless crystals, of melting point 206°–207° C.

Analysis for $C_{14}H_{16}ClN_3O_3$: Calculated: C 54.3 H 5.2 Cl 11.4 N 13.6%. Found: C 54.6 H 5.3 Cl 11.4 N 13.8%.

EXAMPLE 13

Example 2 is repeated, using 2-bromoethyl chloroformate (6.1 g (32.5 millimoles)) in place of methyl chloroformate. After twice recrystallizing the product from methanol/water, 2.4 g (23% of theory) of 6-[p-(2-bromoethoxycarbonylamino)-phenyl]-4,5-dihydro-5-methyl-3(2H)-pyridazinone are obtained as pale yellow crystals of melting point 218°–220° C.

Analysis for $C_{14}H_{16}BrN_3O_3$: Calculated: C 47.5 H 4.6 Br 22.6 N 11.9%. Found: C 48.0 H 4.7 Br 21.5 N 12.0%.

EXAMPLE 14

Example 2 is repeated, using 2,2,2-trichloroethyl chloroformate (6.9 g (32.6 millimoles)) in place of methyl chloroformate. After twice recrystallizing the product from ethanol/water, 3.8 g (34% of theory) of 4,5-dihydro-5-methyl-6-[p-(2,2,2-trichloroethoxycarbonylamino)-phenyl]-3(2H)-pyridazinone are obtained as colorless crystals of melting point 211°–212° C.

Analysis for $C_{14}H_{14}Cl_3N_3O_3$: Calculated: C 44.4 H 3.7 Cl 28.1 N 11.1%. Found: C 44.9 H 3.8 Cl 27.9 N 11.3%.

EXAMPLE 15

Example 1 is repeated, using 2-methoxyethyl chloroformate (5.3 g (38.3 millimoles)) in place of methyl chloroformate. After recrystallizing the product from dimethylformamide/water, 2.5 g (27% of theory) of 4,5-dihydro-6-[p-(2-methoxyethoxycarbonylamino)-phenyl]-3(2H)-pyridazinone are obtained as colorless crystals of melting point 221°–222° C.

Analysis for $C_{14}H_{17}N_3O_4$: Calculated: C 57.7 H 5.9 N 14.4%. Found: C 57.7 H 5.9 N 15.0%.

EXAMPLE 16

Example 2 is repeated, using 2-methoxyethyl chloroformate (6.2 g (44.7 millimoles)) in place of methyl chloroformate. After twice recrystallizing the product from methanol, 1.7 g (19% of theory) of 4,5-dihydro-6-[p-(2-methoxyethoxycarbonylamino)-phenyl]-5-methyl-3(2H)-pyridazinone are obtained as yellowish crystals of melting point 216°–217° C.

Analysis for $C_{15}H_{19}N_3O_4$: Calculated: C 59.0 H 6.3 N 13.8%. found: C 58.9 H 6.2 N 14.1%.

EXAMPLE 17

3.2 g (44.4 millimoles) of (hydroxymethyl)cyclopropane, dissolved in 50 ml of absolute ether, are added dropwise to a stirred solution of 8.8 g (89.0 millimoles) of phosgene in 50 ml of absolute ether at 10°–15° C. The reaction solution is then stirred for 3 hours at room temperature. The excess phosgene is removed by means of a dry stream of nitrogen, and the ether is then removed under reduced pressure at room temperature. The cyclopropylmethyl chloroformate which remains is mixed with 6.0 g (29.5 millimoles) of 6-(p-aminophenyl)-4,5-dihydro-5-methyl-3(2H)-pyridazinone and 100 ml of absolute toluene and the mixture is kept for 7 hours at 80° C. The product is filtered off at 10° C., washed first with toluene and then with water, and recrystallized twice from dimethylformamide/water. 3.0 g (34% of theory) of 6-(p-cyclopropylmethoxycarbonylaminophenyl)-4,5-dihydro-5-methyl-3(2H)-pyridazinone are obtained as colorless crystals of melting point 240°–241° C.

Analysis for $C_{16}H_{19}N_3O_3$: Calculated: C 63.8 H 6.4 N 13.9%. Found: C 63.6 H 6.2 N 14.2%.

EXAMPLE 18

Example 2 is repeated using benzyl chloroformate (5.5 g (32.2 millimoles)) in place of methyl chloroformate. After recrystallizing the product from ethanol/water, 4.2 g (42% of theory) of 6-(p-benzyloxycarbonylaminophenyl)-4,5-dihydro-5-methyl-3(2H)-pyridazinone are obtained as colorless crystals of melting point 168°–169° C.

Analysis for $C_{19}H_{19}N_3O_3$: Calculated: C 67.6 H 5.7 N 12.5%. Found: C 67.6 H 5.7 N 12.7%.

EXAMPLE 19

5.0 g (69.3 millimoles) of cyclobutanol, dissolved in 80 ml of absolute ether, are added dropwise to a stirred solution of 11.5 g (116.3 millimoles) of phosgene in 100 ml of absolute ether at 10°–15° C. The reaction solution is then stirred for 3 hours at room temperature. Thereafter, the excess phosgene is removed by means of a dry stream of nitrogen, and the ether is then removed under reduced pressure at room temperature. The cyclobutyl chloroformate which remains in mixed with 6.0 g (29.5 millimoles) of 6-(p-aminophenyl)-4,5-dihydro-5-methyl-3(2H)-pyridazinone and 180 ml of absolute tetrahydrofuran and the mixture is kept for 20 hours at room temperature and then for 4 hours at 40°–45° C. The product is filtered off at 10° C., washed first with tetrahydrofuran and then with water, and recrystallized from dimethylformamide/water. 2.8 g (31% of theory) of 6-(p-cyclobutoxycarbonylaminophenyl)-4,5-dihydro-5-methyl-3(2H)-pyridazinone are obtained as colorless crystals, of melting point 245°–246° C.

Analysis for $C_{16}H_{19}N_3O_3$: Calculated: C 63.8 H 6.4 N 13.9%. Found: C 63.4 H 6.3 N 14.2%.

EXAMPLE 20

Example 2 is repeated using cyclohexyl chloroformate (7.2 g (44.3 millimoles)) in place of methyl chloroformate. After twice recrystallizing the product from dimethylformamide/water, 3.0 g (31% of theory) of 6-(p-cyclohexoxycarbonylaminophenyl)-4,5-dihydro-5- methyl-3(2H)-pyridazinone are obtained as almost colorless crystals, of melting point 194°–195° C.

Analysis for $C_{18}H_{23}N_3O_3$: Calculated: C 65.6 H 7.0 N 12.8%. Found: C 65.3 H 7.1 N 13.1%.

EXAMPLE 21

Example 2 is repeated using allyl chloroformate (3.9 g (32.3 millimoles)) in place of methyl chloroformate. Recrystallizing the product from methanol gives 3.0 g (35% of theory) of 6-(p-allyloxycarbonylaminophenyl)-4,5-dihydro-5-methyl-3(2H)-pyridazinone as pale yellow crystals, of melting point 206°–207° C.

Analysis for $C_{15}H_{17}N_3O_3$: Calculated: C 62.7 H 6.0 N 14.6%. Found C 62.5 H 5.9 N 14.9%.

EXAMPLE 22

Example 1 is repeated using phenyl chloroformate (5.96 g (38.1 millimoles)) in place of methyl chloroformate. After recrystallizing the product from dimethylformamide/water, 2.4 g (24% of theory) of 4,5-dihydro-6-(p-phenoxycarbonylaminophenyl)-3(2H)-pyridazinone are obtained as almost colorless crystals of melting point 210°–212° C.

Analysis for $C_{17}H_{15}N_3O_3$: Calculated: C 66.0 H 4.9 N 13.6%. Found: C 65.7 H 4.8 N 13.9%.

EXAMPLE 23

Example 2 is repeated using phenyl chloroformate (5.0 g (31.9 millimoles)) in place of methyl chloroformate. After recrystallizing the product from dimethylformamide/water, 3.9 g (41% of theory) of 4,5-dihydro-5-methyl-6-(p-phenoxycarbonylaminophenyl)-3(2H)-pyridazinone are obtained as almost colorless crystals, of melting point 200°–202° C.

Analysis for $C_{18}H_{17}N_3O_3$: Calculated: C 66.9 H 5.3 N 13.0%. Found: C 66.9 H 5.5 N 13.2%.

EXAMPLE 24

5.0 g (24.6 millimoles) of 6-(p-aminophenyl)-4,5-dihydro-5-methyl-3(2H)-pyridazinone, 5.05 g (29.6 millimoles) of m-tolyl chloroformate and 100 ml of absolute toluene are kept at 80° C. for 6 hours. The product is filtered off at 10° C., washed first with toluene and then with water, and recrystallized twice from dimethylformamide/water. 2.5 g (30% of theory) of 4,5-dihydro-5-methyl-6-[p-(m-tolyloxycarbonylamino)-phenyl]-3(2H)-pyridazinone.quarter-hydrate, are obtained as almost colorless crystals, of melting point 166°–167° C.

Analysis for $C_{19}H_{19}N_3O_3 \cdot \frac{1}{4} H_2O$: Calculated: C 66.8 H 5.7 N 12.3 O 15.2%. Found: C 66.6 H 5.7 N 12.2 O 15.0%.

EXAMPLE 25

Example 24 is repeated, using o-methoxyphenyl chloroformate (5.5 g (29.5 millimoles)) in place of m-tolyl chloroformate. After recrystallizing the product from dimethylformamide/water, 3.0 g (35% of theory) of 4,5-dihydro-6-[p-(O-methoxyphenoxycarbonylamino)-phenyl]-5-methyl-3(2H)-pyridazinone are obtained as pale yellow crystals of melting point 185°–186° C.

Analysis for $C_{19}H_{19}N_3O_4$: Calculated: C 64.6 H 5.4 N 11.9%. Found: C 64.6 H 5.3 N 12.2%.

EXAMPLE 26

5.0 g (24.6 millimoles) of 6-(p-aminophenyl)-4,5-dihydro-5-methyl-3(2H)-pyridazinone are dissolved in 150 ml of absolute tetrahydrofuran by heating to 60° C., with stirring. The solution is allowed to cool to room temperature, 5.0 g (24.8 millimoles) of p-nitrophenyl chloroformate are added and the mixture is stirred first for 20 hours at room temperature and then for 5 hours under reflux. It is then concentrated to about 70 ml, 100 ml of water are added and the product is filtered off and recrystallized from dimethylformamide/water at room temperature, giving 6.5 g (72% of theory) of 4,5-dihydro-5-methyl-6-[p-(p-nitrophenoxycarbonylamino)-phenyl]-3(2H)-pyridazinone as yellow crystals, of melting point 177°–178° C.

Analysis for $C_{18}H_{16}N_4O_5$: Calculated: C 58.7 H 4.4 N 15.2%. Found: C 58.5 H 4.4 N 15.2%.

EXAMPLE 27

Example 1 is repeated using S-methyl chlorothioformate (5.3 g (47.9 millimoles)) in place of methyl chloroformate. After recrystallizing the product from dimethylformamide/water, 3.7 g (44% of theory) of 4,5-dihydro-6-(p-methylmercaptocarbonylaminophenyl)-3(2H)-pyridazinone are obtained as colorless crystals, melting, with decomposition, from 275° C. onwards.

Analysis for $C_{12}H_{13}N_3O_2S$: Calculated: C 54.7 H 5.0 N 16.0 S 12.2%. Found C 55.0 H 5.2 N 16.3 S 11.5%.

EXAMPLE 28

Example 2 is repeated using S-methyl chlorothioformate (3.6 g (32.6 millimoles)) in place of methyl chloroformate. After recrystallizing the product from ethanol/water, 3.1 g (38% of theory) of 4,5-dihydro-5-methyl-6-(p-methylmercaptocarbonylaminophenyl)-3(2H)-pyridazinone are obtained as colorless crystals of melting point 214°–216° C., with decomposition.

Analysis for $C_{13}H_{15}N_3O_2S$: Calculated: C 56.3 H 5.5 N 15.2 S 11.6%. Found: C 56.2 H 5.4 N 15.5 S 11.3%.

EXAMPLE 29

Example 2 is repeated using S-ethyl chlorothioformate (4.15 g (33.3 millimoles)) in place of methyl chloroformate. After recrystallizing the product from ethyl acetate, 3.6 g (42% of theory) of 4,5-dihydro-6-(p-ethylmercaptocarbonylaminophenyl)-5-methyl-3(2H)-pyridazinone are obtained as yellowish brown crystals of melting point 212°–213° C., with decomposition.

Analysis for $C_{14}H_{17}N_3O_2S$: Calculated: C 57.7 H 5.9 N 14.4 S 11.0%. Found: C 57.8 H 6.0 N 14.3 S 10.5%.

EXAMPLE 30

Example 2 is repeated, using S-propyl chlorothioformate (4.5 g (32.5 millimoles)) in place of methyl chloroformate. After recrystallizing the product from dimethylformamide/water, 2.8 g (31% of theory) of 4,5-dihydro-5-methyl-6-(p-propylmercaptocarbonylaminophenyl)-3(2H)-pyridazinone are obtained as colorless crystals of melting point 195°–196° C.

Analysis for $C_{15}H_{19}N_3O_2S$: Calculated: C 59.0 H 6.3 N 13.8 S 10.5%. Found: C 59.3 H 6.3 N 14.2 S 10.0%.

EXAMPLE 31

5.0 g (24.6 millimoles) of 6-(p-aminophenyl)-4,5-dihydro-5-methyl-3(2H)-pyridazinone are dissolved in 150 ml of absolute tetrahydrofuran by heating to 60° C., with stirring. The solution is allowed to cool to room temperature, 5.6 g (36.7 millimoles) of 2-methoxypropyl chloroformate are added and the mixture is then stirred for 14 hours under reflux. It is concentrated, water is added and the product is filtered off and recrystallized from dimethylformamide/water, giving 5.7 g (73% of theory) of 4,5-dihydro-6-[p-(2-methoxypropoxycarbonylamino)-phenyl]-5-methyl-3(2H)-pyridazinone as colorless crystals of melting point 173°–175° C.

Analysis for C$_{16}$H$_{21}$N$_3$O$_4$: Calculated: C 60.2 H 6.6 N 13.2%. Found: C 60.4 H 6.5 N 13.4%.

EXAMPLE 32

Example 31 is repeated, using 2-methoxyisopropyl chloroformate instead of 2-methoxypropyl chloroformate. After recrystallizing the product from dimethylformamide/water, 5.8 g (74% of theory) of 4,5-dihydro-6-[p-(2-methoxyisopropoxycarbonylamino)-phenyl]-5-methyl-3(2H)-pyridazinone are obtained as colorless crystals of melting point 208°–210° C.

Analysis for C$_{16}$H$_{21}$N$_3$O$_4$: Calculated: C 60.2 H 6.6 N 13.2%. Found: C 60.4 H 6.5 N 13.6%.

EXAMPLE 33

Example 31 is repeated using 3-ethoxypropyl chloroformate (6.1 g (36.6 millimoles)) in place of 2-methoxypropyl chloroformate. After recrystallizing the product from dimethylformamide/water, 5.8 g (71% of theory) of 4,5-dihydro-6-[p-(3-ethoxypropoxycarbonylamino)-phenyl]-5-methyl-3(2H)-pyridazinone are obtained as colorless crystals of melting point 136°–137° C.

Analysis for C$_{17}$H$_{23}$N$_3$O$_4$: Calculated: C 61.2 H 7.0 N 12.6%. Found: C 61.4 H 6.9 N 12.6%.

EXAMPLE 34

4.3 g (49.9 millimoles) of (hydroxymethyl)cyclobutane are added dropwise to a stirred solution of 10.4 g (105 millimoles) of phosgene in 100 ml of absolute ether, at 0° C. The reaction solution is then stirred for 1 hour at 0° C. followed by one hour at room temperature, and the excess phosgene is removed by means of a dry stream of nitrogen, after which the ether is removed under reduced pressure at room temperature. The cyclobutylmethyl chloroformate which is left (6.9 g) is reacted with 5.0 g (24.6 millimoles) of 6-(p-aminophenyl)-4,5-dihydro-5-methyl-3(2H)-pyridazinone by the method described in Example 31. The reaction mixture is also worked up as described in Example 31. After recrystallizing the product from dimethylformamide/water, 5.5 g (71% of theory) of 6-(p-cyclobutylmethoxycarbonylaminophenyl)-4,5-dihydro-5-methyl-3(2H)-pyridazinone are obtained as colorless crystals of melting point 199°–200° C.

Analysis for C$_{17}$H$_{21}$N$_3$O$_3$: Calculated: C 64.8 H 6.7 N 13.3%. Found: C 64.6 H 6.5 N 13.5%.

EXAMPLE 35

5.9 g (51.7 millimoles) of (hydroxymethyl)-cyclohexane are added dropwise to a stirred solution of 13.0 g (131.4 millimoles) of phosgene in 100 ml of absolute ether at 0°–10° C. The reaction solution is then stirred for 1 hour at 0°–10° C., and then for an hour at room temperature, and the excess phosgene is removed by means of a dry stream of nitrogen, after which the ether is removed under reduced pressure at room temperature. The cyclohexylmethyl chloroformate which is left (8.5 g) is reacted with 5.0 g (24.6 millimoles) of 6-(p-aminophenyl)-4,5-dihydro-5-methyl-3(2H)-pyridazinone by the method described in Example 31. The reaction mixture is also worked up as described in Example 31. After recrystallizing the product first from dimethylformamide/water, then from ethyl acetate/petroleum ether and finally from acetone/water, 2.1 g (25% of theory) of 6-(p-cyclohexylmethoxycarbonylaminophenyl)-4,5-dihydro-5-methyl-3(2H)-pyridazinone are obtained as colorless crystals of melting point 223°–225° C.

Analysis for C$_{19}$H$_{25}$N$_3$O$_3$: Calculated: C 66.5 H 7.3 N 12.2%. Found: C 66.4 H 7.4 N 12.7%.

EXAMPLE 36

4.3 g (49.9 millimoles) of 1-cyclopropylethanol are added dropwise to a stirred solution of 9.9 g (100 millimoles) of phosgene in 100 ml of absolute ether at 0° C. The reaction solution is then stirred for 1 hour at 0° C. followed by one hour at room temperature, and the excess phosgene is removed by means of a dry stream of nitrogen, after which the ether is removed under reduced pressure at room temperature. The 1-cyclopropylethyl chloroformate which is left (6.6 g) is reacted with 5.0 g (24.6 millimoles) of 6-(p-aminophenyl)-4,5-dihydro-5-methyl-3(2H)-pyridazinone by the method described in Example 31. The reaction mixture is also worked up as described in Example 31. After recrystallizing the product first from dimethylformamide/water and then from ethanol/ether, 1.3 g (17% of theory) of 6-[p-(1-cyclopropylethoxycarbonylamino)-phenyl]-4,5-dihydro-5-methyl-3(2H)-pyridazinone are obtained as colorless crystals of melting point 223°–224° C.

Analysis for C$_{17}$H$_{21}$N$_3$O$_3$: Calculated: C 64.8 H 6.7 N 13.3%. Found: C 64.9 H 6.7 N 13.3%.

EXAMPLE 37

6.1 g (49.9 millimoles) of 2-phenylethanol are added dropwise to a stirred solution of 9.8 g (99 millimoles) of phosgene in 100 ml of absolute ether at 0°–5° C. The reaction solution is then stirred for 1 hour at 5°–10° C. followed by one hour at room temperature, and the excess phosgene is removed by means of a dry stream of nitrogen, after which the ether is removed under reduced pressure at room temperature. The 2-phenylethyl chloroformate which is left (9.1 g) is reacted with 5.0 g (24.6 millimoles) of 6-(p-aminophenyl)-4,5-dihydro-5-methyl-3(2H)-pyradazinone by the method described in Example 31. The reaction mixture is also worked up as described in Example 31. After recrystallizing the product from ethyl acetate/petroleum ether, 4.7 g (54% of theory) of 4,5-dihydro-5-methyl-6-[p-(2-phenylethoxycarbonylamino)-phenyl]-3(2H)-pyridazinone are obtained as colorless crystals of melting point 163°–164° C.

Analysis for C$_{20}$H$_{21}$N$_3$O$_3$: Calculated: C 68.4 H 6.0 N 12.0%. Found: C 68.1 H 6.1 N 12.1%.

EXAMPLE 38

6.9 g (49.9 millimoles) of m-methoxybenzyl alcohol are added dropwise to a stirred solution of 9.9 g (100 millimoles) of phosgene in 100 ml of absolute ether at −20° C. The reaction solution is then stirred for 1 hour at −10° C. followed by one hour at room temperature, and the excess phosgene is removed by means of a dry stream of nitrogen, after which the ether is removed under reduced pressure at room temperature. The m-methoxybenzyl chloroformate which is left (11 g) is reacted with 5.0 g (24.6 millimoles) of 6-(p-aminophenyl)-4,5-dihydro-5-methyl-3(2H)-pyridazinone by the method described in Example 31, but stirring the mixture for only 8 hours under reflux. The reaction mixture is worked up as described in Example 31. After recrystallizing the product from propanol, 7.3 g (81% of theory) of 4,5-dihydro-6-[p-(m-methoxybenzyloxycarbonylamino)-phenyl]-5-methyl-3(2H)-pyridazinone are obtained as colorless crystals of melting point 199°–200° C.

Analysis for $C_{20}H_{21}N_3O_4$: Calculated: C 65.4 H 5.8 N 11.4%. Found: C 65.4 H 5.9 N 11.4%.

EXAMPLE 39

A solution of 7.1 g (49.8 millimoles) of m-chlorobenzyl alcohol in 50 ml of absolute ether is added dropwise to a stirred solution of 11.2 g (113 millimoles) of phosgene in 100 ml of absolute ether at −20° C. The reaction solution is then stirred for 1 hour at −10° C. and for a further hour at room temperature, and thereafter the excess phosgene is removed by means of a dry stream of nitrogen and the other is then removed under reduced pressure at room temperature. The m-chlorobenzyl chloroformate which remains (12.0 g) is dissolved in 50 ml of absolute tetrahydrofuran and the solution is added, at room temperature, to a solution, prepared by the method described in Example 31, of 5.0 g (24.6 millimoles) of 6-(p-aminophenyl)-4,5-dihydro-5-methyl-3(2H)-pyridazinone in 100 ml of absolute tetrahydrofuran. The reaction mixture is then refluxed for 14 hours and is worked up by the method described in Example 31. After recrystallizing the product first from chloroform/petroleum ether, then from acetone/water and finally from propanol/water, 4.0 g (44% of theory) of 6-[p-(m-chlorobenzyloxycarbonylamino)-phenyl]-4,5-dihydro-5-methyl-3(2H)-pyridazinone are obtained as colorless crystals of melting point 165°–166° C.

Analysis for $C_{19}H_{18}ClN_3O_3$: Calculated: C 61.4 H 4.9 Cl 9.5 N 11.3%. Found: C 61.5 H 5.0 Cl 9.9 N 11.5%.

EXAMPLE 40

2.8 g (49.9 millimoles) of prop-2-ynol are added dropwise to a stirred solution of 9.9 g (100 millimoles) of phosgene in 100 ml of absolute ether at −10° C. and the reaction solution is then stirred for 1 hour at the same temperature. Thereafter it is stirred for one hour at room temperature and the excess phosgene is then removed by means of a dry stream of nitrogen, after which the ether is removed under reduced pressure at room temperature. The prop-2-ynyl chloroformate which remains (5.2 g) is added, at room temperature, to a solution, prepared by the method described in Example 31, of 5.0 g (24.6 millimoles) of 6-(p-aminophenyl)-4,5-dihydro-5-methyl-3(2H)-pyridazinone in 150 ml of absolute tetrahydrofuran. The reaction mixture is then refluxed for 1 hour and concentrated to about 70 ml. Water is added and the product is filtered off and recrystallized first from ethanol/water, then from acetone/water and finally from ethanol, giving 2.9 g (41% of theory) of 4,5-dihydro-5-methyl-6-[p-(prop-2-ynyloxycarbonylamino)-phenyl]-3(2H)-pyridazinone as colorless crystals, of melting point 204°–205° C.

Analysis for $C_{15}N_{15}N_3O_3$: Calculated: C 63.1 H 5.3 N 14.7%. Found: C 63.3 H 5.4 N 15.0%.

EXAMPLE 41

3.5 g (49.9 millimoles) of 1-methylprop-2-ynol are added dropwise to a stirred solution of 9.9 g (100 millimoles) of phosgene in 100 ml of absolute ether at −10° C. The reaction solution is then stirred for 1 hour at −10° C. followed by one hour at room temperature, and the excess phosgene is removed by means of a dry stream of nitrogen, after which the ether is removed under reduced pressure at room temperature. The 1-methylprop-2-ynyl chloroformate which is left (5.9 g) is reacted with 5.0 g (24.6 millimoles) of 6-(p-aminophenyl)-4,5-dihydro-5-methyl-3(2H)-pyridazinone by the method described in Example 31. The reaction mixture is also worked up as described in Example 31. After recrystallizing the product first from ethanol/water, then from ethyl acetate/petroleum ether and finally from dimethylformamide/water, 1.7 g (23% of theory) of 4,5-dihydro-5-methyl-6-[p-(1-methylprop-2-ynyloxycarbonylamino)-phenyl]-3(2H)-pyridazinone are obtained as colorless crystals of melting point 206°–207° C.

Analysis for $C_{16}H_{17}N_3O_3$: Calculated: C 64.2 H 5.7 N 14.0%. Found: C 64.2 H 5.8 N 14.2%.

Examples of formulations prepared in a conventional manner:

| 1. Tablets: | |
| --- | --- |
| Active compound | 10 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |
| | 240 mg |

The active compound is moistened with a 10% strength aqueous solution of the polyvinylpyrrolidone, forced through a 1.0 mm mesh sieve and dried at 50° C. The granules obtained are mixed with the polyethylene glycol (mean molecular weight 4,000), hydroxypropylmethylcellulose, talc and magnesium stearate, and the mixture is pressed to give tablets each weighing 240 mg.

| 2. Example of dragees: | |
| --- | --- |
| Active compound | 10 mg |
| Lactose | 90 mg |
| Corn starch | 60 mg |
| Polyvinylpyrrolidone | 6 mg |
| Magnesium stearate | 1 mg |
| | 167 mg |

The mixture of the active compound, lactose and corn starch is moistened with an 8% strength aqueous solution of the polyvinylpyrrolidone, granulated by passing through a 1.5 mm mesh sieve, dried at 50° C. and forced through a 1.0 mm mesh sieve. The granules thus obtained are mixed with magnesium stearate and the mixture is pressed to give dragee cores. These cores are then coated in a conventional manner with a shell essentially consisting of sugar and talc.

We claim:

1. A compound of the formula I

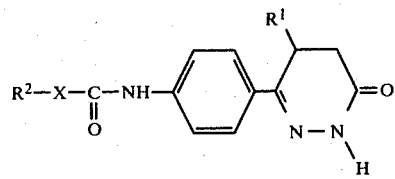

where X is oxygen or sulfur, $R^1$ is methyl and $R^2$ is alkyl of 1 to 4 carbon atoms which is unsubstituted or contains up to three chlorine, bromine or fluorine atoms, alkyl of 2 to 4 carbon atoms which is substituted by alkoxy of 1 to 3 carbon atoms which is separated from X by not less than two carbon atoms, alkyl of 1 to 3 carbon atoms which is substituted by cycloalkyl which has 3 to 6 carbon atoms in the ring and may or may not carry one or two alkyls of 1 to 3 carbon atoms, alkyl of 1 to 4 carbon atoms which is substituted by phenyl which itself is unsubstituted or substituted by one to three identical or different substituents chosen from alkyl of 1 to 3 carbon atoms, alkoxy of 1 to 3 carbon atoms, halogen, trifluoromethyl and nitro, cycloalkyl of 3 to 6 carbon atoms in the ring, which is unsubstituted or substituted by one to four alkyls of 1 to 4 carbon atoms, alkenyl of 3 to 5 carbon atoms, alkynyl of 3 to 5 carbon atoms or phenyl which is unsubstituted or substituted by one to three identical or different substituents chosen from alkyl of 1 to 4 carbon atoms, alkoxy of 1 to 4 carbon atoms, halogen, trifluoromethyl, cyano and nitro.

2. A therapeutic agent for treating thrombotic diseases which comprises: a pharmaceutically acceptable carrier or diluent for oral administration and an effective amount of a compound of the formula I of claim 1.

3. A method of treating thrombotic diseases which comprises: orally administering in dosage form to the subject to be treated the composition described in claim 2, each dose containing from 1 to 100 mg. of active compound.

4. A compound of the formula I as claimed in claim 1, where $R^1$ is methyl and $R^2$ is alkyl of 1 to 4 carbon atoms which is unsubstituted or carries up to 3 substituents chosen from chlorine, bromine and fluorine, or is cycloalkyl which has 3 to 6 carbon atoms in the ring and is unsubstituted or substituted as specified in claim 1, or is benzyl in which the phenyl ring is unsubstituted or substituted as specified in claim 1, or is alkynyl of 3 to 5 carbon atoms.

* * * * *